United States Patent [19]

Fogarty

[11] Patent Number: 4,774,949
[45] Date of Patent: Oct. 4, 1988

[54] DEFLECTOR GUIDING CATHETER

[76] Inventor: Thomas J. Fogarty, 770 Welch Rd., Palo Alto, Calif. 94304

[21] Appl. No.: 504,141

[22] Filed: Jun. 14, 1983

[51] Int. Cl.⁴ .............................................. A61B 1/00
[52] U.S. Cl. ..................................... 128/348.1; 128/4; 128/5
[58] Field of Search ........................ 128/348.1, 4, 5, 6, 128/7; 604/158, 159, 160, 171, 172, 264, 268, 280, 283, 284, 772, 52, 53, 96, DIG. 26

[56] References Cited

U.S. PATENT DOCUMENTS

| | | | |
|---|---|---|---|
| 1,861,769 | 6/1932 | Wappler | 128/348.1 |
| 2,024,982 | 12/1935 | Scott | 128/348.1 |
| 3,605,750 | 9/1971 | Sheridan et al. | 128/348 |
| 3,978,863 | 9/1976 | Fettel et al. | 128/348.1 |
| 4,323,071 | 4/1982 | Simpson et al. | 128/349 B X |
| 4,454,887 | 6/1984 | Kruger | 128/172 |

FOREIGN PATENT DOCUMENTS 2063553 7/1971 Fed. Rep. of Germany.
3115192 4/1982 Fed. Rep. of Germany.

Primary Examiner—William H. Grieb
Attorney, Agent, or Firm—Limbach, Limbach & Sutton

[57] ABSTRACT

A catheter is provided with a lumen which extends along most of the length of the catheter and then curves outwardly to terminate in a port for the passage of guide wires and catheters through the lumen into branch arteries.

5 Claims, 1 Drawing Sheet

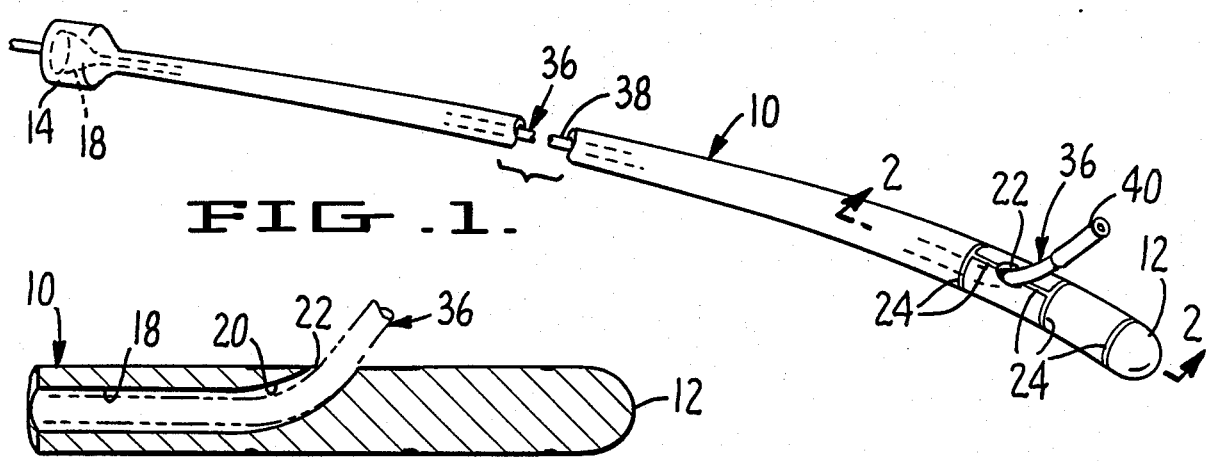
FIG. 1.
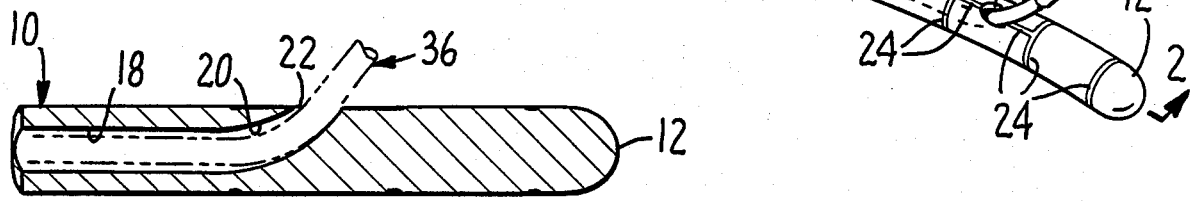
FIG. 2.
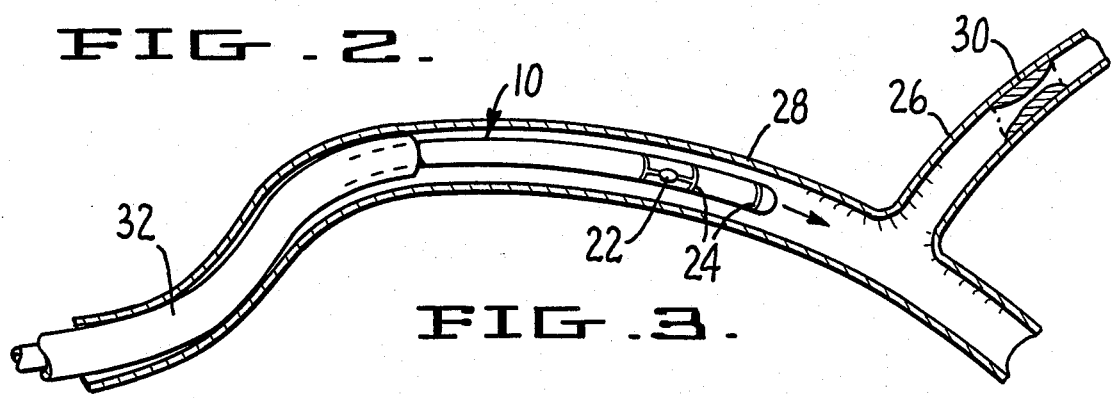
FIG. 3.
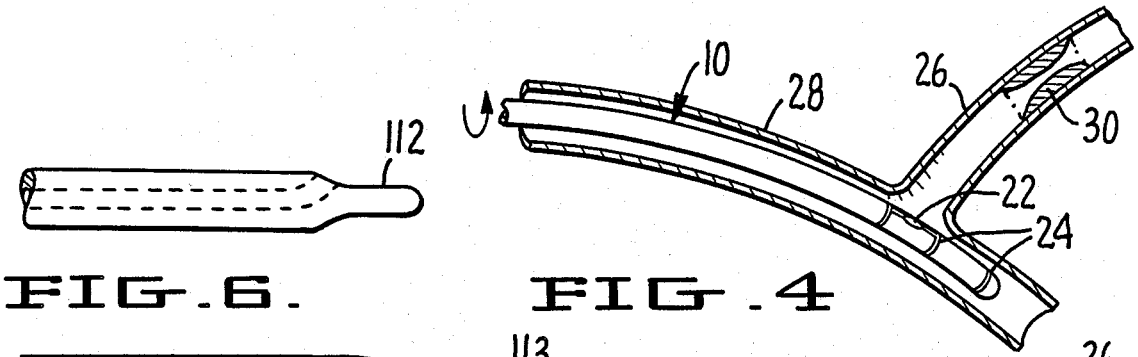
FIG. 4.
FIG. 6.
FIG. 7.
FIG. 8.
FIG. 9.
FIG. 5

DEFLECTOR GUIDING CATHETER

BACKGROUND OF THE INVENTION

1. Field of the Invention

The field of the invention is catheter equipment for use in connection with the placement of catheters in conduits for such purposes as dilatation, occlusion, infusion, removal, and visualization, i.e. for use in connection with basically any catheterization procedure.

More specifically, the invention relates to a primary or deflector guiding catheter means and method for guiding and emplacing secondary catheters in areas where routine access is difficult or impossible by conventional means. Secondary catheters include, among others, dilatation, infusion, perfusion, diagnostic and occlusion embolectomy catheters. The primary catheter of the invention may be also used to guide and emplace guide wires instead of secondary catheters.

2. Description of the Prior Art

I am unaware of any prior art relating to deflector guiding catheters.

SUMMARY OF THE INVENTION

The subject deflector guiding or primary catheter has a guide lumen for passage of a secondary catheter. For the greater part of the length of the guide catheter the lumen extends axially along the catheter. As the lumen approaches the distal end of the catheter it smoothly curves from axial to angular orientation and terminates in an outlet port which can be readily disposed in registry with the inlet end of an angulation artery. The shape and curvature of the distal portion of the lumen serve to support the secondary catheter during advancement and to prevent backup movement of the secondary catheter during placement, dilatation and/or extrusion.

This deflector guiding catheter may be used in connection with catheterization procedures generally in which the problem is presented of transferring the catheter from one arm to the other of a bifurcation.

DESCRIPTION OF THE DRAWING

FIG. 1 is a view in perspective of the deflector guiding catheter.

FIG. 2 is an enlarged view taken along lines 2—2 of FIG. 1.

FIG. 3 shows the deflector guiding catheter in the act of being moved along an artery to a bifurcation arm of the artery.

FIG. 4 is a view like FIG. 3 but showing the catheter positioned with its side delivery port in registry with the bifurcation arm.

FIG. 5 is a view like FIG. 4 showing a dilatation catheter extending into the bifurcation arm from the side delivery port of the deflector guiding catheter.

FIGS. 6–9 show a variety of alternative tip configurations for the deflector guiding catheter.

DESCRIPTION OF THE PREFERRED EMBODIMENTS

The guiding catheter comprises a flexible tubular body 10 having a rounded distal end 12 and a proximal guide fitting 14 having a funnel-shaped guide socket 16 to facilitate introduction of guide wires and other catheters into the catheter. The catheter 10 is provided with a lumen 18 which extends axially of the catheter for the greater part of the length of the catheter and is then smoothly curved along a distal portion 20 which teminates in a side delivery port 22.

The guiding catheter is provided with radio-opaque markings to indicate the location of tip 12, port 22 and to assist in the alignment orientation of port 22 and the mouth of a bifurcation artery 26. The markings are designated by reference number 24.

FIG. 3 indicates, for example, a coronary artery 28 having the bifurcation 26. Within the latter is the stenotic lesion 30 for treatment.

The deflector guiding catheter 10 is worked along the artery 28 through a guide catheter 32 which may be similar to guide catheter 21 in U.S. Pat. No. 4,323,071.

The circular guide markings 24 will indicate when the port 22 is located at the mouth of the branch artery 26. The catheter 10 may then be rotated about its longitudinal axis to bring the port 22 into opposition registry with the mouth of the branch artery, the line markings 24 along the extended long axis of the port 22 being used as controls in this regard. This brings the deflector guiding catheter 10 and the main and branch arteries 28, 26 into the relationship shown in FIG. 4. The main body of the catheter 10 may be provided with a braided, or relatively stiff but flexible, construction so as to satisfactorily transmit the torques required to orientate the port 22 with the branch artery, while the distal tip 12 of catheter 10 can be made soft and pliable.

When the FIG. 4 positional relationship between catheter 10 and the main and branch arteries has been achieved, a dilatation catheter 36 comprising flexible tubular body 36 and a distal balloon element 40 is fed along the lumen of catheter 10 and through the side delivery port 22 of catheter 10 into the branch artery adjacent lesion 30, as shown in FIG. 5. Other types of catheters as well as guide wires may be fed along the primary catheter 10. The balloon 40 is preferably of the invertible-evertable type having the property of everting out of the catheter without substantial radial expansion during the initial inflation stage and having the property of then being radially expansible during a second stage of inflation. Such a balloon is thus everted into the lesion 30 and thereafter radially expanded to dilate the lesion and open up the artery to increase blood flow.

In the embodiment of FIG. 6, the deflector guiding catheter is provided with a tip 112 of smaller diameter to enable the tip to fit more readily into the smaller distal branch of artery 28 beyond the branch artery 26.

The embodiment of the deflector guiding catheter in FIG. 7 is provided with a guide wire extension 113 which is fixedly attached to the end of the catheter. The guide wire extension serves as a floppy guide for the fitting of the end of the catheter into the smaller distal branch of artery 28.

In the embodiment of FIGS. 8–9 the catheter is provided with an axial extension 119 of lumen 18. At the confluence of these passages an elastomer plug 121 is fixedly positioned. The plug 121 may be pierced with a guide wire 123. Thus, this embodiment of the deflector guiding catheter can be placed over a guide wire for emplacement. After emplacement, and prior to emplacement of the secondary catheter, the guide wire 123 is removed and the passage through the plug 121 for the wire 123 becomes closed by a self-sealing action.

It will be apparent from FIG. 2 that the smoothly curved configuration of lumen portion 20 serves to support the dilatation catheter 36 during advancement of the latter relative to catheter 10 and prevents backup movement of the dilatation catheter relative to catheter 10 during placement, dilatation and/or extrusion of the former.

It should be pointed out that a guide wire may be passed through the catheter 10 followed by introduction of the dilatation catheter along the guide wire. Also, the linear extrusion dilatation catheter 36 can have its balloon element 40 everted or extruded from within the catheter 10 rather than first having the balloon element located beyond catheter 10 as shown in the drawing.

What is claimed is:

1. A deflector guiding catheter adapted to guide guide wires and other catheters through tortuous conduits and deflectingly transfer them laterally from the conduits, said catheter comprising: an elongated flexible tubular body member proportioned for passage through a tortuous conduit, said body member being sufficiently pliable to bend and conform to the shape of the conduit; guide wire and catheter accommodation and movement-guiding means embodied in said body member, said means comprising a lumen having major and minor portions, the major portion extending longitudinally along said body member for the greater portion of the length thereof, the minor portion being at the distal end portion of said body member, being smoothly curved outwardly from said major portion, and terminating in an angularly directed outlet port.

2. The catheter of claim 1, said outlet port being oval in shape, the major axis of the oval and the longitudinal axis of said body member being disposed in substantially a common plane.

3. The catheter of claim 1, said body member being provided with radio-opaque markings whereby the distal end of the body member and the outlet port may be located and oriented relative to arterial bifurcations.

4. A method for moving a dilatation catheter from a tortuous conduit into a branch conduit comprising: directing a flexible tubular body member through the tortuous conduit to conform the body member to the shape of said conduit and emplace the body member at a bifurcation site, said body member being sufficiently pliable to conform to the shape of the tortuous conduit and having a passageway which extends along the conduit and then changes direction in accordance with the included angle relationship between said tortuous conduit and said branch conduit to terminate in an angularly directed outlet port; orienting said body member so that said outlet port is in registry with the inlet end of said branch conduit; and moving a catheter through said body member along said passageway and into said branch conduit.

5. A method for moving a linear extrusion balloon element of a dilatation catheter from a main artery into a branch artery for treatment of a stenotic lesion in said branch artery comprising: directing a flexible tubular body member through the main artery to conform the body member to the shape of said main artery and emplace the body member at an artery bifurcation site, said body member being sufficiently pliable to conform to the shape of the artery and having a passageway which extends along the artery and then changes direction in accordance with the included angle relationship between said main artery and branch artery to terminate in an angularly directed outlet port; moving said dilatation catheter along said passageway so that said balloon element is directed at said branch artery through said port; and linearly extruding said balloon element through said port and into treatment relation to said stenotic lesion.

* * * * *